(12) United States Patent
Van Saarloos

(10) Patent No.: US 7,364,575 B2
(45) Date of Patent: Apr. 29, 2008

(54) APPARATUS AND PROCEDURE FOR ULTRAVIOLET LASER ABLATION

(75) Inventor: Paul Phillip Van Saarloos, Karrinyup (AU)

(73) Assignee: CustomVis plc., Westminster (AU)

( * ) Notice: Subject to any disclaimer, the term of this patent is extended or adjusted under 35 U.S.C. 154(b) by 0 days.

(21) Appl. No.: 11/088,286

(22) Filed: Mar. 24, 2005

(65) Prior Publication Data

US 2005/0171514 A1 Aug. 4, 2005

Related U.S. Application Data

(63) Continuation of application No. 10/204,188, filed as application No. PCT/AU01/00136 on Feb. 14, 2001, now Pat. No. 7,090,669.

(30) Foreign Application Priority Data

Feb. 14, 2000 (AU) .................... PQ5594

(51) Int. Cl.
*A61F 9/009* (2006.01)
(52) U.S. Cl. .............................. 606/5; 606/4
(58) Field of Classification Search ............... 128/898; 606/4–5
See application file for complete search history.

(56) References Cited

U.S. PATENT DOCUMENTS

| | | | |
|---|---|---|---|
| 4,994,058 A * | 2/1991 | Raven et al. ............ | 606/5 |
| 5,112,328 A * | 5/1992 | Taboada et al. .......... | 606/4 |
| 5,133,708 A | 7/1992 | Smith | |
| 5,318,044 A * | 6/1994 | Kilmer et al. ........... | 128/898 |
| 5,484,432 A * | 1/1996 | Sand ..................... | 606/5 |
| 5,520,679 A * | 5/1996 | Lin ....................... | 606/5 |
| 5,586,980 A * | 12/1996 | Kremer et al. .......... | 606/4 |
| 5,616,139 A | 4/1997 | Okamoto | |
| 6,026,816 A * | 2/2000 | McMillan et al. ....... | 128/898 |

FOREIGN PATENT DOCUMENTS

| | | |
|---|---|---|
| EP | 0 818 181 | 1/1998 |
| WO | 89/06519 | 7/1989 |
| WO | 95/15134 | 6/1995 |
| WO | 95/30392 | 11/1995 |

OTHER PUBLICATIONS

Ren et al., Ablation of the Cornea and Synthetic Polymers Using a UV (213nm) Soldi Sate Laser, IEEE Journal of Quantum Electronics Dec. 1990.*

Dair et al., Investigation of Corneal Ablation Efficiency Using Ultraviolet 213nm Solid State Laser Pulses, IOVS, Oct. 1999.*

* cited by examiner

*Primary Examiner*—Henry M. Johnson, III
(74) *Attorney, Agent, or Firm*—Merchant & Gould P.C.

(57) ABSTRACT

Apparatus for performing ultraviolet laser ablation of a surface, eg. an eye surface, including a laser delivery system (7) having a laser source (1) for generating a laser beam (2) and optics for applying the laser beam to the surface to be ablated, means (20, 20') for providing a compatible liquid (32) in contact with the surface (4a) to be ablated, in a position whereby said laser beam (2) is applied to said surface through the liquid, wherein the laser beam is of a wavelength that substantially is not absorbed by the liquid.

10 Claims, 4 Drawing Sheets

APPARATUS AND PROCEDURE FOR ULTRAVIOLET LASER ABLATION

CROSS-REFERENCE TO RELATED APPLICATIONS

This application is a continuation of application Ser. No. 10/204,188 filed Mar. 19, 2003, now U.S. Pat. No. 7,090,669 which is the National Stage of Application PCT/AU01/00136 filed Feb. 14, 2001, and which applications are incorporated herein by reference.

FIELD OF THE INVENTION

This invention relates generally to ultraviolet laser ablation, used for example in laser eye treatment, and is of particular, though by no means exclusive, utility in ophthalmic refractive surgery operations such as laser in situ keratomiluesis (LASIK).

BACKGROUND ART

A number of refractive surgery operations involve the removal of small amounts of corneal tissue to effect a refractive change. In earlier developed laser operations such as photorefractive keratectomy (PRK), the epithelial layer is manually removed and then Bowman's membrane and part of the stroma are ablated by laser energy. This operation can lead to unwanted side effects, such as corneal haze, and is not suitable for higher refractive errors.

A more recently developed refractive operation called laser in situ keratomiluesis (LASIK) maintains the integrity of the epithelial layer and Bowman's membrane. A flap of tissue is displaced from the anterior cornea and a minute amount of tissue in the shape of a lens is removed from the stromal bed or from the underside of the lenticule, by way of laser ablation. The corneal lenticule or "flap" is then replaced to its original position creating an optical correction.

The LASIK refractive surgery procedure produces fewer side effects and quicker healing relative to PRK, as the epithelium and Bowman's membrane are left intact. Because the epithelium is generally not touched in LASIK, there is also less pain for the patient and the healing process is enhanced with LASIK, presumably because the healing region is protected: there is moreover only one type of tissue involved in the healing process instead of two. It is thought that about 80% of laser eye surgery is now LASIK rather than PRK.

Notwithstanding these advantages, a known problem with LASIK is that the corneal surface formed by the microkeratome cut is relatively rough and this reduces the patient's vision for watching the fixation light, important for maintaining the pupil correctly aligned, and furthermore reduces the vision of the eye tracker device used to guide the laser delivery system. It is thought that these two issues contribute to the known outcome that the statistical success rate of LASIK is similar to PRK despite the enhanced healing process.

It is therefore an object of the invention, in a preferred application, to address the aforementioned problems with LASIK in an effort to more consistently achieve the outcome expected of LASIK relative to PRK. It is a more general object to provide an improved ultraviolet laser ablation procedure.

SUMMARY OF THE INVENTION

The invention involves recognition of the benefits of using particular wavelengths for the ablation, and of carrying out the ablation in a manner which departs in one notable respect from the conventional approach.

The most commonly used wavelength in ultraviolet laser ablation, and in refractive laser surgery in particular, is 193 nm, the wavelength of the pulsed beam derived from a conventional excimer laser. A problem issue with this wavelength has always been that it is very strongly absorbed by water and the presence of any stray fluid, including natural eye tissue fluid, dramatically alters the ablation process. There is therefore a requirement to minimise liquid in the ablation region. Thus, physiological saline solution conventionally added to wash away the area in front of the eye before the treatment must be collected and extracted prior to the ablation, even though saline solution may be added again afterwards for washing purposes.

It has been appreciated by the present inventors that the absorption by physiological saline solution of 193 nm laser light is so high as to be not accurately measurable using conventional varying depth measurements. The absorption of the 213 nm band is so low as to be capable of accurate measurement only with difficulty (ie. large columns (depths) of solution).

The invention entails the application of a physiologically compatible liquid in contact with the surface to be ablated, and the use for the ablation of a laser beam of a wavelength that is substantially not absorbed by the liquid.

The invention provides, in a first aspect, apparatus for performing ultraviolet laser ablation of a surface, eg. an eye surface, including a laser delivery system having a laser source for generating a laser beam and optics for applying the laser beam to the surface to be ablated, means for providing a compatible liquid in contact with the surface to be ablated, in a position whereby said laser beam is applied to said surface through the liquid, wherein the laser beam is of a wavelength that substantially is not absorbed by the liquid.

In a further aspect, the invention provides a method of performing ultraviolet laser ablation of a surface, eg. an eye surface, including having a compatible liquid in contact with the surface to be ablated, and applying a laser beam to the surface through the liquid to effect ablation of the surface with the laser beam, wherein the laser beam is of a wavelength that substantially is not absorbed by the liquid.

The liquid may be provided by retaining the liquid in contact with the surface to be ablated.

For laser ablation of an eye surface, the liquid is a physiologically compatible liquid. In one embodiment, the physiologically compatible liquid retained in contact with the surface to be ablated is natural liquid of the eye. In an alternative embodiment, the liquid is introduced to the eye and the retaining means may then include cap or ring means for contacting the surface to be ablated to retain liquid within the cap means.

An advantageous wavelength suitable for the purposes of the invention is about 213 nm. Such a laser beam may be produced from a solid state laser using frequency doubling and mixing crystals. A suitable arrangement, utilising a Q-switched neodymium:YAG laser as the primary source, is described, for example in international patent publication WO 99/04317.

Where the liquid retaining means is a cap or ring device, it preferably further includes overlying wall means spaced from the eye surface which has a lens through which the ablating laser beam is directed. The lens is preferably arranged to allow the patient to see the fixation light in reasonable focus and to provide an even better optical surface to see with than the water alone.

The retaining means may include means for holding it against the surface to be ablated. Such may be a suitable suction or vacuum arrangement.

In an advantageous application of the invention, the laser ablation is a step in a LASIK procedure. For this purpose, the apparatus may further include microkeratome means for cutting a flap from the cornea to expose an interior surface to be ablated. In this application, a common ring may serve as both the microkeratome guide ring and the liquid retaining means of the invention.

In this application, the method may further include cutting a flap from the cornea to expose an anterior surface to be ablated.

BRIEF DESCRIPTION OF THE DRAWINGS

The invention will be further described, by way of example only, with reference to the accompanying diagrams, in which.

Figure 1:
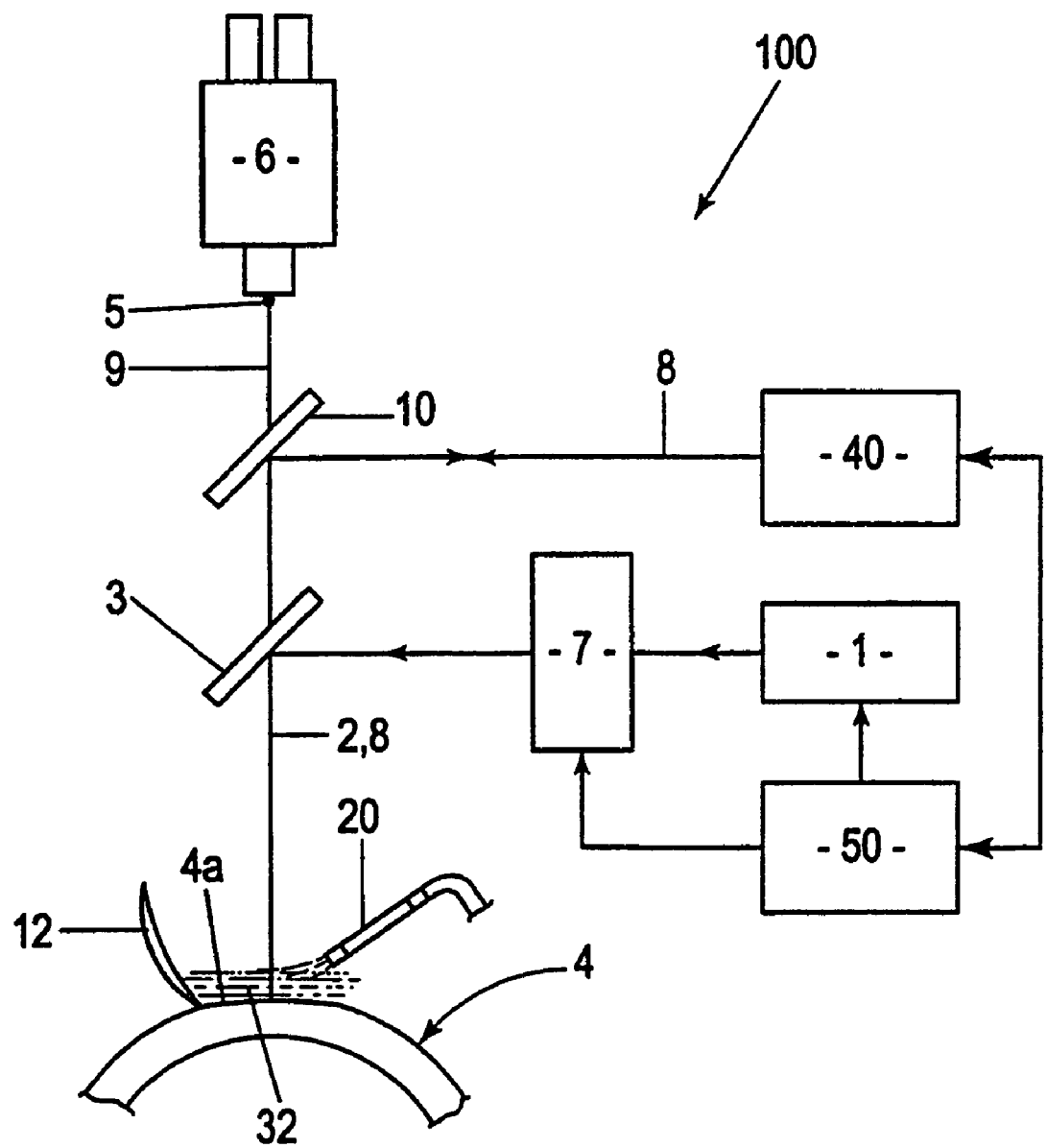
FIG. 1 depicts an arrangement for performing LASIK according to a first embodiment of the invention, shown at the point at which the liquid has been applied to the exposed corneal surface in preparation for the ablation step.

In the illustrated surgical laser system 100, a surgical laser source 1, preferably a frequency converted solid state laser or any other laser emitting a suitable wavelength as aforedescribed, eg. 213 nm, directs a surgical laser beam 2, via delivery system 7, and laser mirror 3 (which is transparent to infra-red and visible light) towards the cornea of an eye 4 to be treated. To ensure that gross eye movements are restricted, the patient's gaze is fixated on a flashing LED 5 located beneath a surgical microscope 6 with which the surgeon views the procedure. To compensate for decentration of the pupil through head, eye or saccadic movement, or a loss of patient fixation, there is provided an eye tracking system generally indicated at 40. System 40 may typically generate a collimated infra-red beam 8 which is directed via beamsplitter 10 onto the optic axis of the eye coincident with main laser beam 2 and the fixation line of sight 9.

Laser source 1 may comprise a solid state laser and a plurality of frequency doubling and mixing crystals for deriving the said laser beam from the output beam of the laser. A suitable arrangement, utilising a Q-switched neodymium:YAG laser as the primary source, is described, for example in international patent publication WO 99/04317.

A LASIK procedure has already commenced on eye 4 and a microkeratome (not shown) has been utilised to part and draw back a surface flap 12 of the cornea, including the epithelium. In a first embodiment depicted in FIG. 1, the operator now uses a supply tube 20 to apply and maintain a liquid layer 32 of physiologically compatible solution over exposed corneal surface 4a. This is the inverse of the conventional step in excimer laser refractive surgery (at 193 nm) of removing the solution from in front of the corneal surface prior to ablation. In the ablation step according to the invention, the ablating beam 8 is applied through liquid 32, to ablate surface 4a. The beam is dimensioned by delivery system 7, and scanned in accordance with a predetermined control schedule in computer control 50, which also manages other components.

The physiologically compatible saline solution may typically be dextran, a fluid commonly used to avoid swelling of tissue, or balanced salt solution.

The interposed retained liquid 32 helps cool the corneal tissue because there is substantially no absorption of the ablating light: the liquid remains cool and this helps reduce the limited degree of tissue damage relative to the damage known to occur to a small degree in excimer ablation.

A further advantage of the liquid overlay 32 is that there is no gas plume. The gas plume is the vaporised material produced by the ablation which in conventional excimer ablation hovers over the ablated surface after each pulse and diminishes the effect of the next succeeding pulse in a non-uniform fashion, despite the application of suction to remove the plume. Some surgeons also suspect that the plume has made them sick. To avoid the excessive build-up of ablation products dissolved in the fluid, it is preferred that the fluid be replaced or flows over the ablation surface during the procedure.

Where the material to be ablated is not tissue there would be similar advantages to do the ablation under a layer of water. This includes the cooling effect of the fluid and the softening of the ablation process that would help protect delicate structures or materials beneath the ablation site. One such non-tissue application is the restoration of art works by laser ablation.

Figure 2:
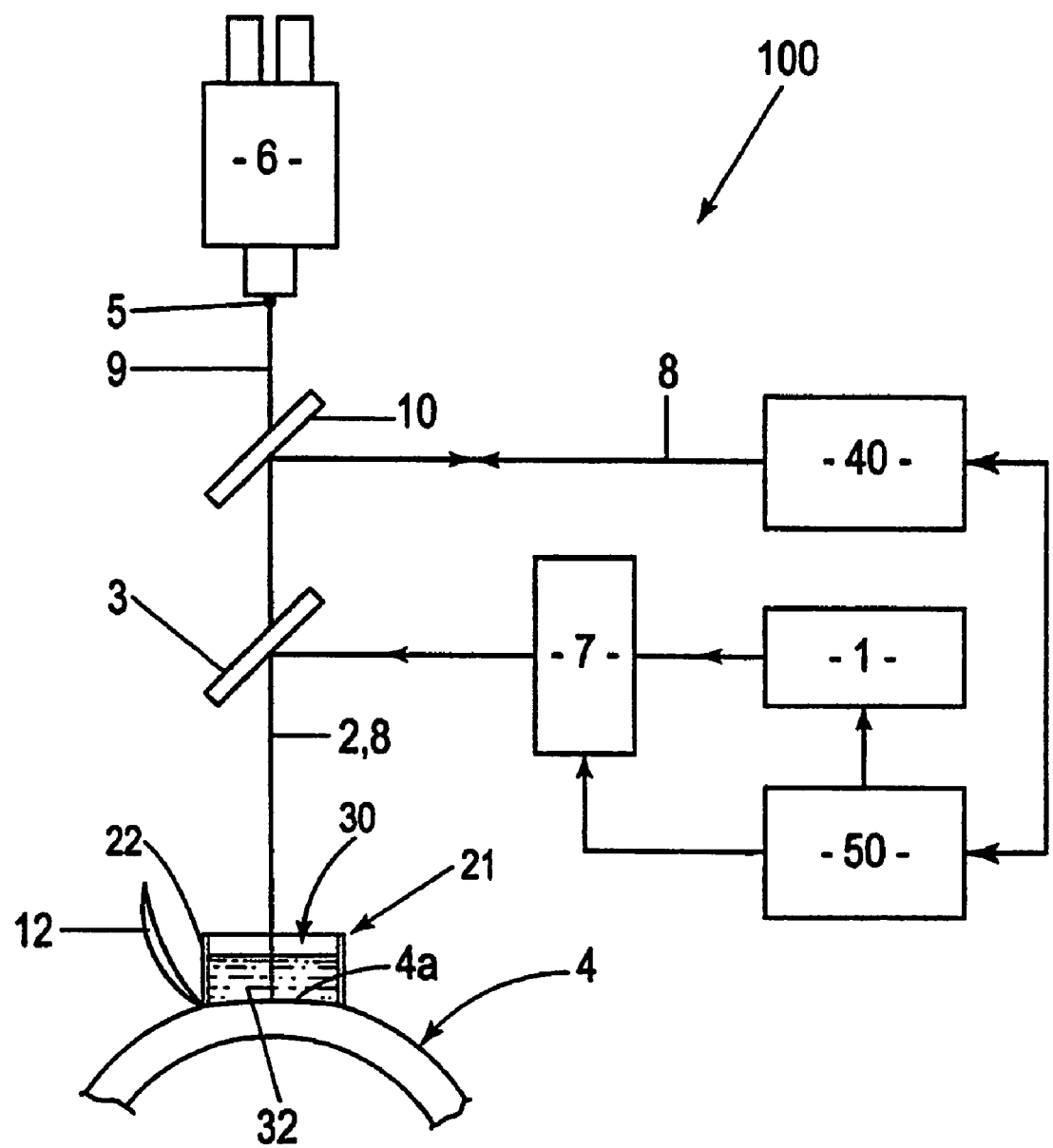
FIG. 2 is a view similar to FIG. 1 of an alternative embodiment.
Figure 3:
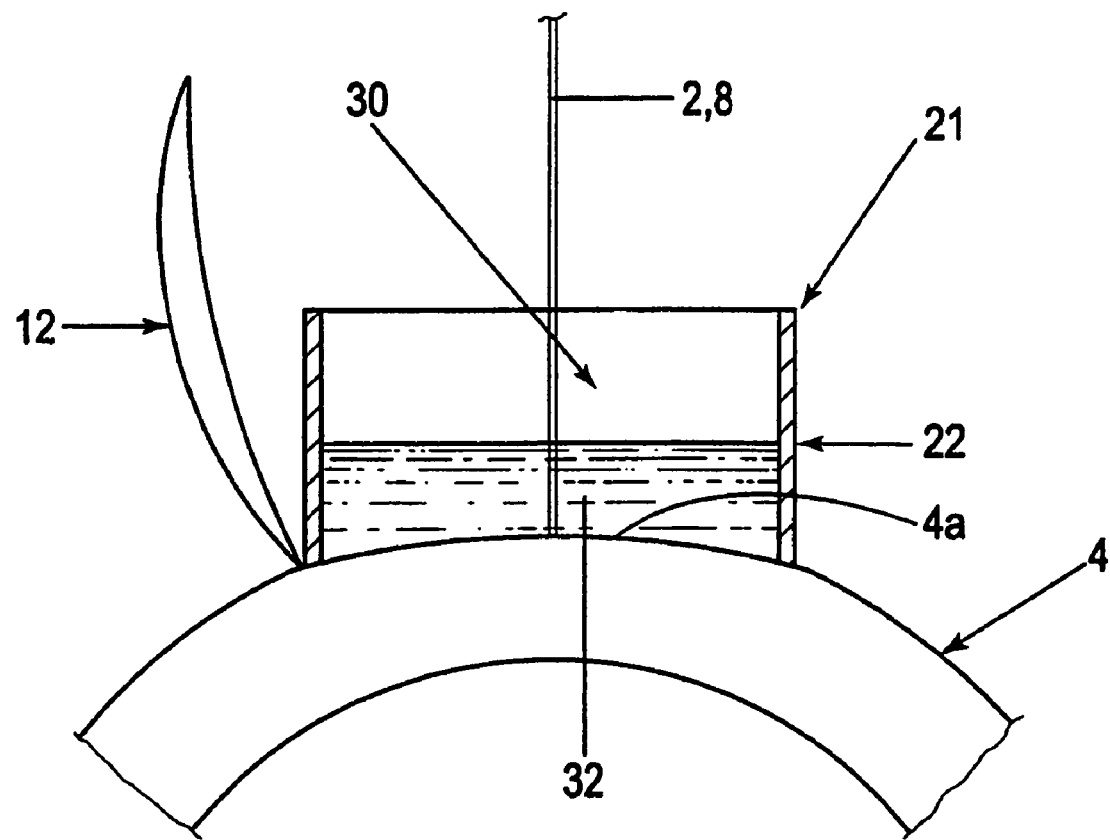
FIG. 3 is an enlargement of part of FIG. 2.
Figure 4:
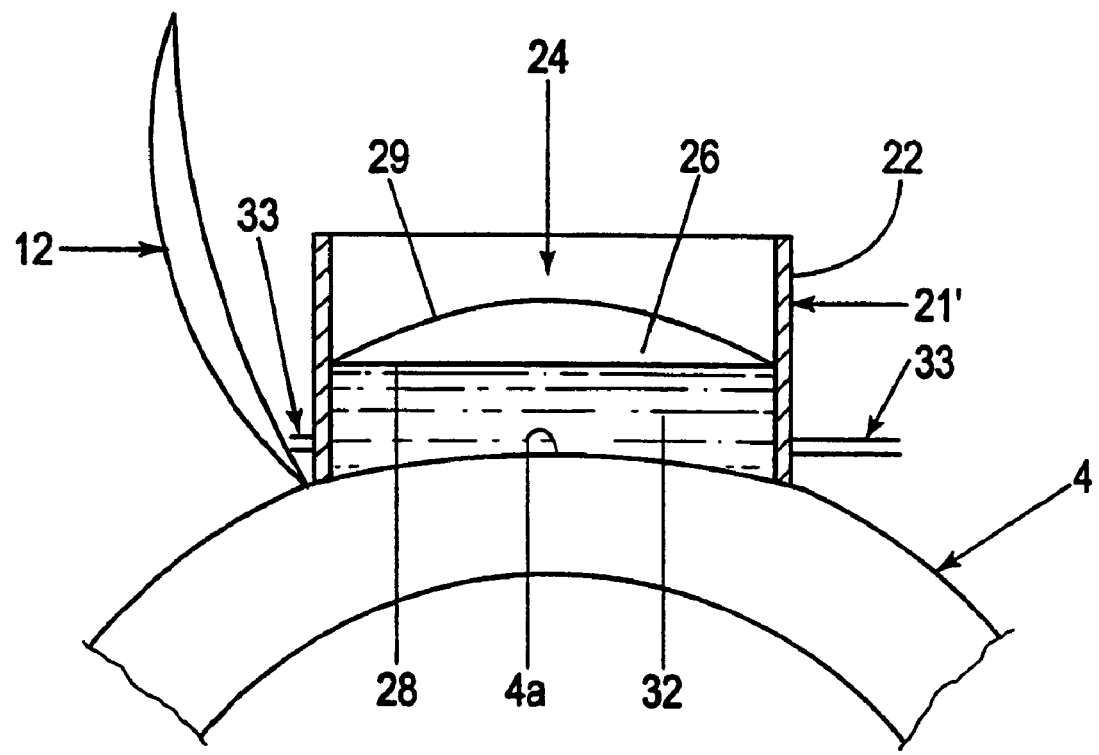
FIG. 4 is a view similar to FIG. 3 showing a modified embodiment.

In alternative embodiments illustrated in FIGS. 2 and 3 and in FIG. 4, a cap or ring device 21 is positioned to confine and define the overlying layer of liquid 32.

The cap or ring device 21 is generally cylindrical and is applied to the exposed corneal surface 4a by the operator once flap 12 has been excised and drawn aside. The cylindrical body 22 of the ring device is open at its forward rim in contact with surface 4a and, in the simple embodiment shown in FIGS. 2 and 3, also open at its rear. Alternatively (FIG. 4), the ring 21' may be closed at its rearward end by a wall 24 including or consisting of a lens 26 pre-fitted within ring 21', or applied in situ. Lens 26 preferably has an optically flat interior face 28 as illustrated, though it could be convex or concave, and a convex exterior face 29.

Ring 21, 21' defines a chamber 30 which is filled with physiologically compatible saline solution 32, introduced, for example, through the tubes 33 (FIG. 4), which allow the fluid to flow over the surface.

In the embodiment of FIG. 4, because of the interposed liquid 32, the presence of lens 30, and the fact that the refractive index of corneal tissue is similar to water, it is thought that the patient may be able to see fixation light 5 more clearly, and thereby to maintain a fixated gaze more reliably, while tracker system 40 is better able to clearly view the pupil.

Any other practical method of introducing the fluid to the surface 4a, eg a pipette, may of course be used.

The invention claimed is:

1. Apparatus for performing ultraviolet laser surface ablation of an eye surface for effecting refractive correction of the eye, including a laser source for generating a pulsed laser beam having a wavelength of about 213 nm. and a delivery system configured for applying the laser beam as a refractive surgery laser beam to the eye surface to be ablated, a discrete ring or cap device separate from said delivery system, the ring or cap device adapted to contact said eye surface after it is exposed by execising and drawing back a surface flap of the eye, the ring or cap device retaining a physiologically compatible liquid in contact with the eye surface to be ablated, physiologically compatible liquid in a position whereby said refractive surgery laser beam is applied to said eye surface through the liquid, wherein said delivery system is configured to scan the laser beam through said ring or cap device over said eye surface to effect ablation of said eye surface with the laser beam, wherein the liquid cools said eye surface as it is ablated.

2. Apparatus according to claim 1 wherein said laser source includes a solid state laser and a plurality of frequency doubling and mixing crystals for deriving the said laser beam from an output beam of the laser.

3. Apparatus according to claim 1 wherein said cap or ring means further includes overlying wall means spaced from said eye surface which has a lens through which said refractive surgery laser beam is directed.

4. Apparatus according to claim 1 wherein said ring or cap device further includes means for holding it against the eye surface to be ablated.

5. Apparatus according to claim 1 adapted whereby the laser ablation is a step in a LASIK procedure, and further including microkeratome means for cutting a flap from the cornea to expose an interior surface to be ablated.

6. Apparatus according to claim 5 wherein a common ring serves both as a guide ring for the microkeratome and as means for retaining liquid in contact with the eye surface to be ablated.

7. Apparatus according to claim 1 further including a light viewable by the eye.

8. Apparatus according to claim 7 further including an eye tracking system including means to direct a beam onto the eye surface through said liquid retained by said ring or cap device.

9. Apparatus according to claim 1 further including an eye tracking system including means to direct a beam onto the eye surface through said liquid retained by said ring or cap device.

10. Apparatus for performing ultraviolet laser surface ablation of an eye surface for effecting refractive correction of the eye, including a laser delivery system having a laser source for generating a pulsed laser beam having a wavelength of about 213 nm and optics for applying the pulsed laser beam to the eye surface to be ablated, means for providing a physiologically compatible liquid in contact with the surface to be ablated, in a position whereby said pulsed laser beam is applied to said surface through the liquid to effect ablation of the surface with the laser ablation is a step in LASIK procedure, and further including microkeratome means for cutting a flap from the cornea to expose an interior surface to be ablated, wherein a common ring serves both as a guide ring for the microkeratome and as means for retaining liquid in contact with the surface to be ablated.

* * * * *